United States Patent
Artigas Verde et al.

(10) Patent No.: US 7,641,344 B2
(45) Date of Patent: Jan. 5, 2010

(54) DEVICE AND METHOD TO DETERMINE THE CONTRAST SENSITIVITY OF AN INDIVIDUAL'S VISUAL SYSTEM

(75) Inventors: Jose Maria Artigas Verde, Burjassot (ES); Pascual Capilla Perea, Burjassot (ES); Maria Jose Luque Cobija, Burjassot (ES); Santiago Albert Seseña, L'Hospitalet del Llobregat (ES); Verónica Márquez Pérez, L'Hospitalet del Llobregat (ES); Adelina Felipe Marcet, Burjassot (ES)

(73) Assignees: Universitat de Valencia, Burjassot (ES); Indo Internacional, S.A., Sant Cugat del Valles (ES)

( * ) Notice: Subject to any disclaimer, the term of this patent is extended or adjusted under 35 U.S.C. 154(b) by 168 days.

(21) Appl. No.: 11/572,800

(22) PCT Filed: Jul. 26, 2005

(86) PCT No.: PCT/ES2005/070109

§ 371 (c)(1),
(2), (4) Date: Jan. 26, 2007

(87) PCT Pub. No.: WO2006/024687

PCT Pub. Date: Mar. 9, 2006

(65) Prior Publication Data

US 2007/0236666 A1    Oct. 11, 2007

(30) Foreign Application Priority Data

Jul. 29, 2004    (ES)    ................. 200401961

(51) Int. Cl.
A61B 3/02    (2006.01)

(52) U.S. Cl. ...................................... 351/239; 351/237
(58) Field of Classification Search .................. 351/239
See application file for complete search history.

(56) References Cited

U.S. PATENT DOCUMENTS

| 3,861,790 | A  | * | 1/1975 | Tamura ..................... 351/237 |
| 5,539,482 | A  |   | 7/1996 | James et al. |
| 6,623,118 | B2 |   | 9/2003 | De La Rosa |
| 2003/0081176 | A1 |   | 5/2003 | Stewart |
| 2003/0163060 | A1 | * | 8/2003 | Maddess et al. ............. 600/544 |
| 2003/0174284 | A1 |   | 9/2003 | Stewart |

FOREIGN PATENT DOCUMENTS

| WO | 9529627 A | 11/1995 |
| WO | 0069327 A | 11/2000 |

* cited by examiner

Primary Examiner—Jordan M. Schwartz
Assistant Examiner—James C Jones
(74) Attorney, Agent, or Firm—Peter B. Scull; Kristina M. Kalan; Berenbaum Weinshienk PC

(57) ABSTRACT

A device to determine the contrast sensitivity of an individual's visual system by means of a series of tests in a measurement session, comprising a means for producing real time digital images, corresponding to modulated visual stimuli; and a display means for presenting said images to an individual's eye, wherein said stimuli may be modulated around an average stimulus in any direction of the color space and may be configured in their spatial and temporal characteristics for each measurement session. Said stimuli are usually chosen in the cardinal directions of the color space and respond to a sinusoidal grid pattern with spatial and temporal modulation, and with a two dimensional gaussian envelope.

18 Claims, 3 Drawing Sheets

DEVICE AND METHOD TO DETERMINE THE CONTRAST SENSITIVITY OF AN INDIVIDUAL'S VISUAL SYSTEM

The present device and method determine the contrast sensitivity of an individual's visual system by a series of tests during a measurement session, by producing real time digital images corresponding to modulated visual stimuli, and displaying these images to an individual's eye.

BACKGROUND OF THE INVENTION

Visual information travels from the retina to the primary visual cortex or striatum following two parallel paths referred to as magnocellular and parvocellular ways. These ways have their origin in the ganglionar cells called M and P, respectively. 75% of magnocellular way cells (referred to as MX) are linearly responsible whereas 25% of said cells (referred to as My) are nonlinear. All the parvocellular cells are linearly responsible.

There is much evidence proving that the detection of a purely chromatic contrast pattern, whether it be red-green or blue-yellow, is mediated by cells with spectral opponency belonging to the parvocellular way. Therefore, this way would be revealed as the physiological support for detection of chromatic contrasts in the whole space-time domain. Detection of an achromatic contrast pattern is much more controversial, although some studies point to the magnocellular way as the physiological support for detection of chromatic contrasts in the corner of low spatial frequencies and high temporal frequencies within the space-time domain.

A large variety of pathologies result from major injuries in one of these ways, and possibly in both. The origin of the pathology can be found in the retina, in the optic nerve, chiasma or any other site in the visual ways and even in visual cortex. Whatever the extent and the magnitude of the damage caused, it has been proven that contrast sensitivity on the damaged way will be altered. In any case, it is important to know which pathologies impair the Magno, which the Parvo, and which both, and in each case, which is the most suitable strategy for detecting a reduction in sensitivity on the damaged way or ways.

From the above it follows that when only the Magno is damaged by a pathology, a reduction of sensitivity in the visual system should be revealed by using an achromatic pattern of low spatial frequencies and high temporal frequencies. Nevertheless, an injury in the Parvo will result in a reduction of sensitivity in an wide set of spatial-temporal conditions with achromatic patterns and in any spatial-temporal conditions with modulated isoluminant patterns in any directions of the space color, specifically, the cardinal directions of the red-green or blue-yellow mechanisms. It has been not sufficiently proven which of the predictable reductions is primary in the progress of the pathology nor which is the one of highest magnitude. It also has not been sufficiently proven what deterioration is primary and more significant when both Magno and Parvo visual ways are injured by pathology. On the other hand, it is well known that the possibilities of making a good patient diagnosis are significantly enhanced if scanning of the whole retina and not only of the fovea is performed, that is, if what in the clinical language is referred to as campimetry is performed. In its more traditional form, campimetry consists of measuring, at each position of the field of sight, the threshold luminance so that a simple white circular spot can be detected on a background with a certain luminance, also white. However, in this type of campimetry, sensitivity losses are detected when a significant amount of ganglionar cells, for example in glaucoma, have already been damaged.

In recent years, notable efforts have been made to improve expectations in campimetric scanning. In the technique referred to as SWAP (Short Wavelength Automated Perimetry) a threshold is determined for detecting a blue circular spot on a yellow background. It has been shown that the detection of a spectral stimulus of a certain wavelength on a white background is mediated by ganglionar cells that are more sensitive for that wavelength. Blue spot campimetry improves the results that would be obtained traditionally with white on white campimetry. But a yellow background will increase the probability that the blue stimulus is detected by the blue-yellow channel. Although SWAP has substantially improved the features of the campimetries on a white background, is not still a technique free of problems. For example, it is well known that the response of a chromatic or achromatic mechanism is not isolated by an incremental paradigm (that is, a stimulus represented on a background), since it simultaneously entails a variation in the luminance and a variation in the color.

On the other hand, it has been proposed that the detection of a sinusoidal achromatic pattern in space and time with suitable frequencies may be capable of isolating the response of magnocellular way cells. These cells are affected, like the cells with blue-yellow opponency, by different pathologies, including glaucoma. If spatial frequency is particularly low and temporal frequency is particularly high, the pattern is perceived as if spatial frequency was twice as much as it actually is. It has been suggested that this phenomenon, referred to as frequency doubling, is attributable to My cells' nonlinear behavior. The technique related to frequency doubling observation is referred to as FDT (Frequency Doubling Technology).

US patent U.S. Pat. No. 5,065,767 discloses a method according to which a patient is presented a sinusoidal grid pattern which contrast is modulated to a frequency ranging from 10 to 50 Hz. The patient initially observes a spatial frequency doubling in this grid. Contrast resistance is gradually being reduced until a threshold value is reached at which the patient stops observing the frequency doubling. In patients with glaucoma this threshold can be as much as twice the contrast an observer considered as normal would need.

On the other hand, U.S. Pat. Nos. 6,068,377 and 6,227,668 provide methods that expand upon the above idea, in the sense that the frequency doubling would also occur with any pattern where the color palette consists of mixtures of complementary colors, particularly, blue and yellow mixtures. The pattern must be periodic in space and time and, as in the achromatic frequency doubling, spatial frequency must be low (not greater than 5 cycles/degree) and temporal frequency must be high (not smaller than 7 cycles/seconds). My cells are probably also responsible for this phenomenon, so a stimulus capable of producing a chromatic frequency doubling would a priori gather a number of potentially useful conditions for evaluating of problems that simultaneously involve deteriorations in Magno cells and Parvo cells with blue-yellow opponency. Nevertheless, it has not been proven at the moment that this type of campimetry is more effective than campimetry based upon achromatic frequency doubling.

Also with regard to frequency doubling, PCT application WO 95/29627 discloses a method that includes measuring, for different areas of a patient's field of sight, the minimum contrast with which this patient can still perceive an achromatic frequency doubling. This method detects early damage caused in the retina by glaucoma that affects only one part of the patient's field of sight.

In any case, a combination of two more tests may improve the early diagnosis of ocular pathologies, because some tests can detect before others the same sight defects caused by different pathologies. For example, sometimes an optic neuropathy may be identified earlier by means of stereophotographies than by detecting a sensitivity loss; or, on the contrary, a sensitivity loss is often detected in glaucoma first by SWAP or FDT tests. In any case, both SWAP and FDT, with some advantage for FDT, is revealed to be quite effective as early indicators of sensitivity loss in glaucoma.

DETAILED DESCRIPTION

The device described herein is a high performance device which may provide a very wide range of measurements and tests of the type being proposed so far, including chromatic and achromatic frequency doubling, and which also may answer questions still open to discussion, such as whatever a blue-yellow stimulus producing frequency doubling is more effective for detecting glaucoma or a particular pathology that a pattern with blue-yellow modulation in any other area of the spatial-temporal domain, or if a stimulus with the spatial frequency and the temporal frequency in the area of maximum sensitivity first highlights the presence of a problem, or if achromatic patterns in the area of maximum sensitivity are equal or more effective for detecting a problem in the parvocellular way than a pattern with blue-yellow modulation, or if certain pathologies entailing injuries in cells with opponency red-green can be detected with greater effectiveness by stimuli with this class of modulation.

According to one aspect of the device, contrast sensitivity of the visual system may be determined by means of a device that runs a series of tests in a measurement session, such that the stimuli of these tests may be modulated around an average stimulus in any direction of the color space and may be configured in spatial and temporal characteristics for each measurement session. Said sensitivity may be determined in the whole spatial-temporal domain and in any direction of the color space, that is a form of representation of the responses of the mechanisms A, T and D, where A is a non opponent or achromatic mechanism, and T and D are mechanisms with red-green and blue-yellow opponency, respectively.

These stimuli may be chosen in the directions of the color space in which only one of the mechanisms A, T or D is able to respond to the stimulus, which are the so-called cardinal directions of the color space.

By default, this average stimulus may correspond to the white color of the displaying means.

Advantageously, stimuli may be sinusoidally time-modulated.

In one embodiment, these stimuli may correspond to a sinusoidal grid pattern with spatial and temporal modulation.

In one embodiment, a sinusoidal grid may be modulated, in turn, through a two dimensional gaussian envelope.

The spatial frequency of this pattern may be selected from 0 to 20 cycles/degree and its spatial modulation may be along a horizontal direction. The temporal frequency of the pattern may be between about 0 to about 30 cycles/second. Length of each stimulus is about 0 to about 5 seconds.

In one embodiment, the colors included in the modulated stimuli in a particular direction of the color space may be extracted from a 256 color palette generated for a particular direction.

One embodiment may incorporate a camera for recording the eye position during a test of the measurement session.

One embodiment may incorporate a device to hold the individual's head and gaze as steady as possible in each test of the measurement session. The device may incorporate a chin rest with occluder and support for lenses.

In one embodiment, the individual's field of sight may be examined up to 20° vertically and 30° horizontally around a fixation point and the fixation point may be moved up to 20° vertically and 30° horizontally. In this way, by varying the position of the fixation point it is possible to examine the individual's field of sight up to 40° in vertical and 60° in horizontal.

In order to examine the individual's field of sight, one embodiment may divide the field of sight into in sectors, establishing a specific sector for the fovea.

In one embodiment a means for producing images and a displaying means may incorporate a computing system with a central processing unit and memory.

The memory may include: a measurement session configuration and control routine; a measurement session results repository; a repository of results obtained for individuals with no visual pathologies, referred to as standard observers; a visual pathology diagnosis routine from the results of the measurement session and said standard observers; and a displaying routine of said results and said diagnosis.

The routine of measurement session configuration and control may include: a stimuli configuration subroutine; a measurement method configuration subroutine; a spatial and temporal randomization subroutine of stimuli representation; a stimuli amplitude selection subroutine; and a real time recording subroutine of the results of the measurement session.

There may also be for indicating detection, if this is the case, on the part of the individual about a spatial-temporal change with respect to average stimulus.

Contrast sensitivity may be determined by a method comprising the use of a device as the one described in the foregoing paragraphs of this section.

During the measurement session the individual may be able to indicate detection, if this is the case, about a spatial-temporal change with respect to the average stimulus.

In one embodiment, in order a detection is counted the individual has to indicate it after a period of time from the appearance of the stimulus but before its disappearance.

During the measurement session the position in which each test stimulus is presented to the eye may be randomly varied and the pause between one stimulus and the following one may also be randomly varied.

The device may determine the individual's blind spot position and size. A high luminance, substantially point shaped, short visual stimulus may be presented to the individual's eye successively moving in horizontal and vertical directions, with the individual being able to press a push button when the stimulus is visible to him/her, so that the blind spot position and size may be calculated from the area in which the individual does not respond to the stimulus.

The measurement session may include: presenting a stimulus with the maximum possible value of the amplitude; repeating stimulus presentation by dividing the amplitude successively by about 2 as long as a stimulus is detected by the individual, that is, until reversal occurs; repeating stimulus presentation multiplying successively by about $2^{1/2}$ the amplitude from non detection until the stimulus has been detected again by the individual, that is, until a new reversal occurs; carrying out both preceding steps but applying a division or multiplication factor of about $2^{2^{-n}}$, respectively, with n being the reversal number; finishing the session after about 4 reversals or about 20 presentations; allocating the last amplitude value detected to the threshold; and determining contrast sensitivity as the inverse of said threshold.

The measurement session may include the semi-random presentation of control stimuli of false positives, false negatives and fixation loss.

The method may use an algorithm for selecting the parameters of each test based upon the results of previous measurement sessions.

DETAILED DESCRIPTION OF THE DRAWINGS

Figure 1:
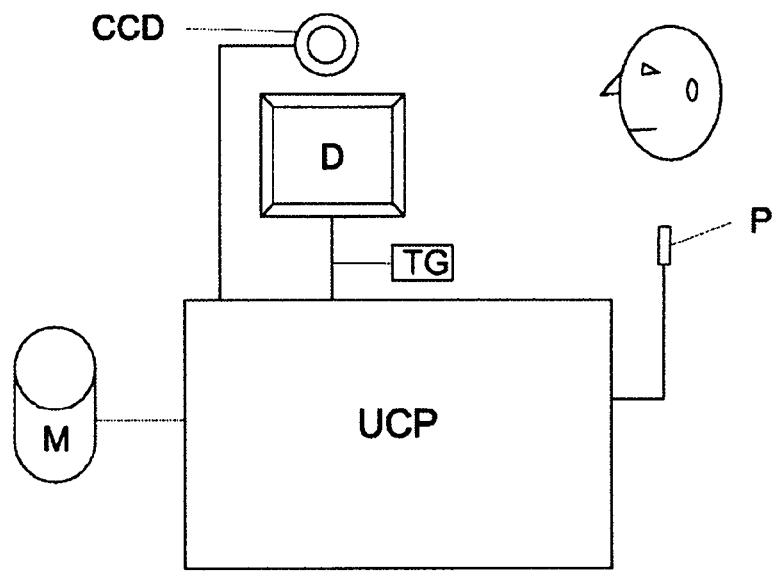
FIG. 1 is a diagrammatic depiction of the device.

As it can be seen from FIG. 1, the device may have a central processing unit UCP, a memory M, a graphics card of at least about 14 bits TG, about 17 to about 21 inch screen D, a CCD camera for automatic control of fixation, a chin rest with support for lenses and occluder, a monitor for displaying results, a keyboard, a push button P and a color printer. All these elements are built in a single body.

In more detail, said device may include a computer system with the following:

A central processing unit UCP;
A graphics card TG for producing real time digital images corresponding to modulated visual stimuli.
A Display D for presenting images to an individual's eye.
A device P for indicating detection, if this is the case, on the part of the individual of variations in said stimuli.
A memory M or hardware for instructions and data including:
 1. A measurement session configuration and control routine; this routine invoices:
 A stimuli configuration subroutine
 A measurement method configuration subroutine
 An individual's blind spot position and size determination subroutine
 A spatial and temporal randomization of individual stimuli displaying subroutine
 A stimuli amplitude selection subroutine
 A measurement session results real time recording subroutine.
 2. A repository or data base of measurement session results.
 3. A repository of results obtained for individuals with no visual pathologies, referred to as standard observers.
 4. A diagnosis routine of a visual pathology from measurement session results and standard observers.
 5. A routine for displaying a measurement session and diagnosis results.

The device may be operated in two ways: one way may have a default menu and another way may have a menu for performing a customized configuration of the characteristics of the stimulus and the trial parameters.

Features of the device configuration and operation are described below in different sections.

About Stimuli Chromatic Characterization

A stimulus modulated around an average may be described by means of the amplitude $\Delta A$, $\Delta T$, $\Delta D$ from the responses in the mechanisms A, T and D, respectively, where A is a non opponent or achromatic mechanism and T and D are mechanisms with red-green and blue-yellow opponency, respectively. This form of representation is referred to as space color or opponent modulation space. It may be applied according to an equation as follows:

$$\begin{pmatrix} \Delta A \\ \Delta T \\ \Delta D \end{pmatrix} = \begin{pmatrix} K_A & & \\ & K_T & \\ & & K_D \end{pmatrix} \begin{pmatrix} L_0 & M_0 & 0 \\ L_0 & -L_0 & 0 \\ -L_0 & -M_0 & L_0 + M_0 \end{pmatrix} \begin{pmatrix} \frac{\Delta L}{L_0} \\ \frac{\Delta M}{M_0} \\ \frac{\Delta S}{S_0} \end{pmatrix}$$

where $K_A$, $K_T$, $K_D$ are constants that define the units of measurement in each mechanism.

Figure 3:
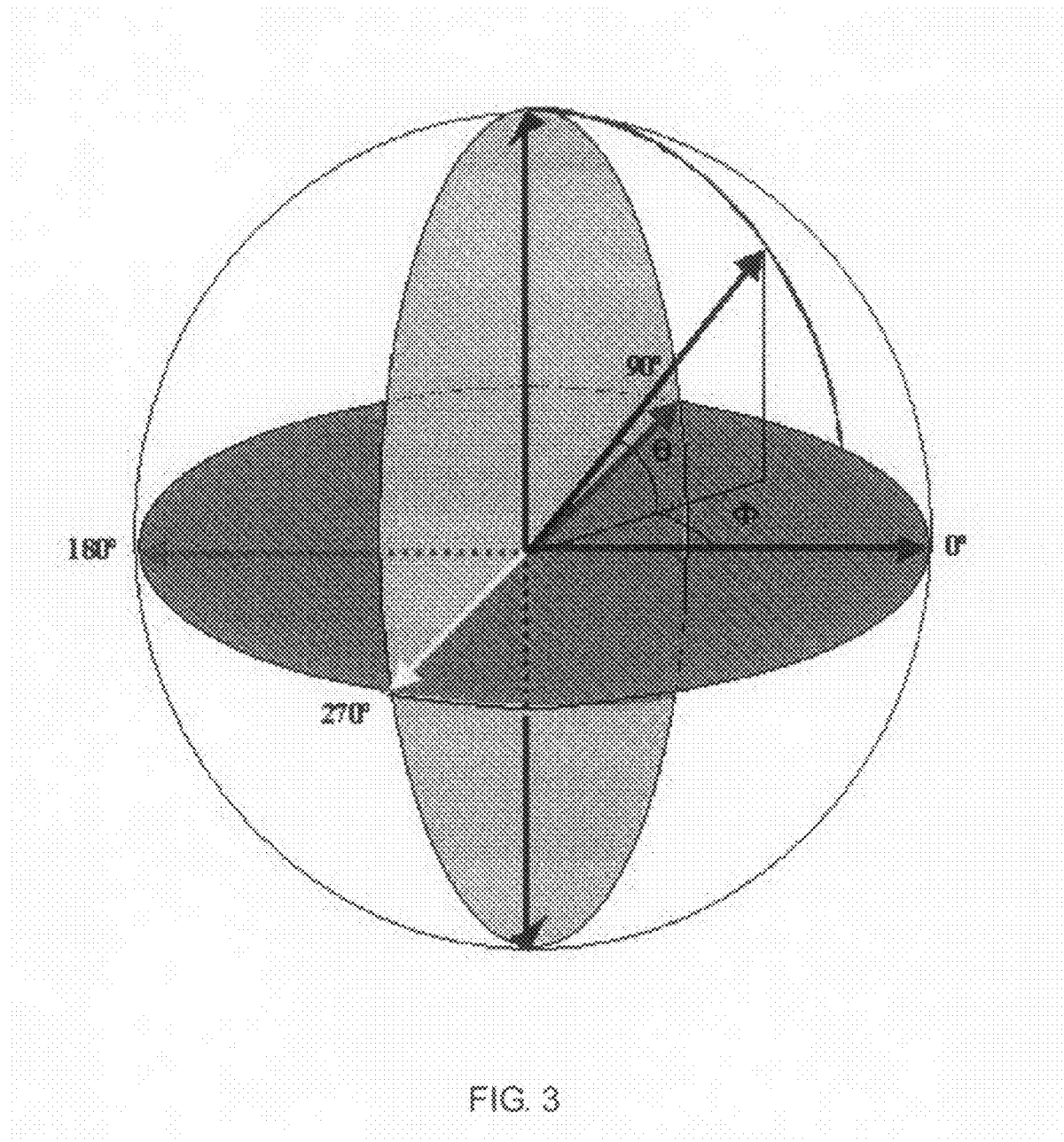
FIG. 3 is a depiction of color space cardinal directions.

The device allows contrast sensitivity to be evaluated with stimuli modulated around an average stimulus in any direction of the color space. Default generated modulation directions are those in which only one of the mechanisms responds. These directions are referred to as cardinal directions of the color space and are depicted in FIG. 3.

About the Range of Colors that Can Be Reproduced by the Screen and the Way Palettes Are Generated Maximum stimuli amplitude values isolating each mechanism that can be reproduced by a particular screen must be explicitly measured for each screen. When the user selects a cardinal direction an about 256 equidistant color palette is automatically generated by a program designed for this purpose in the isolated mechanism response, within the range of the maximum and minimum values allowed by the display screen. The number of colors in the palette that will be used for generating a particular image will depend upon the spatial frequency pattern and the image size.

About Definition of Sensitivity

Contrast absolute threshold may be measured for detecting a particular sinusoidally modulated stimulus in a cardinal direction of the color space. With luminance or achromatic grids, the so-called Michelson contrast is traditionally used as a metric, which is defined as follows:

$$C = \frac{Y_{MAX} - Y_{MIN}}{Y_{MAX} + Y_{MIN}} = \frac{\Delta Y}{Y_0}$$

where $Y_{MAX}$ and $Y_{MIN}$ are the maximum and minimum luminances of the sinusoid, $\Delta Y$ is the amplitude and $Y_0$ is the average luminance. Contrast sensitivity may then be defined as follows:

$$CSF(fx, ft) = \frac{1}{C_{UMB}(fx, ft)}$$

This metric may be maintained for grids isolating the achromatic channel, only by substituting amplitude, $\Delta Y$, and average luminance, $Y_0$, for $\Delta A$ and $A_0$, respectively. However, might not be applied in the chromatic channels since average values $T_0$ and $D_0$ are approximately zero; they would be in fact strictly zeros if modulation would be done around an equienergetic white. Alternatively, a threshold may be estimated as the minimum value of the amplitude for which there is detection. Since the average around which it is modulated could be the same for all the measures, amplitude thresholds are proportional to contrast thresholds. Therefore, a pseudo CSF in channel A may be defined as follows:

$$CSF(fx, ft) = \frac{1}{\Delta A_{UMB}(fx, ft)}$$

And analogously, in channels T and D:

$$CSF(fx, ft) = \frac{1}{\Delta T_{UMB}(fx, ft)}$$

$$CSF(fx, ft) = \frac{1}{\Delta D_{UMB}(fx, ft)}$$

About Spatial and Temporal Characterization of Stimuli

The patterns generated by default through the device are space and time sinusoidal grids, with the vertical bands established by default, and with a two dimensional gaussian envelope. The spatial-temporal profile of this pattern, referred to as Gabor stimulus, may be described as follows:

$$\begin{pmatrix} \Delta A(x,t) \\ \Delta T(x,t) \\ \Delta D(x,t) \end{pmatrix} = \begin{pmatrix} \Delta A_0 \\ \Delta T_0 \\ \Delta D_0 \end{pmatrix} sen2\pi f_e x\, sen2\pi f_t t \cdot \exp\left\{-\frac{(x^2+y^2)}{\sigma^2}\right\} rect\left(\frac{x}{a}, \frac{y}{a}\right) g(t)$$

where:

$$g(t) = \begin{cases} e^{-\frac{(t-t_1)^2}{2\sigma^2}} & \text{if } 0 \leq t \leq t_1 \text{ ms} \\ 1 & \text{if } t_1 < t \leq t_2 \text{ ms} \\ e^{-\frac{(t-t_2)^2}{2\sigma^2}} & \text{if } t_2 < t \leq t_e \text{ ms} \end{cases}$$

The number of pixels per cycle necessary to generate the desired frequency may be rounded off to the closer integer value by the developed program and therefore not all the generated frequencies may correspond with the desired frequency. Therefore, for the generated frequency to correspond with the desired one, frequencies which can be generated with a whole number of pixels per cycle may be requested. This condition involves that the requested frequencies be sampling frequency divisors. On the other hand, for the generated grid profile to be as sinusoidal as possible, the particularly even divisors of the sampling frequency should be included among the frequencies fulfilling the above requirement, which is, by default, about 16 cycles by degree at the observation distance.

The conditions to be fulfilled by temporal frequencies may be the same as for spatial frequencies. The frequency of the temporal sampling is, by default, about 72 Hz.

Spatial and temporal frequencies generated by the device are about 0, 0, 5, 2, 4, 8 and 16 cycles/degree in the spatial domain, and about 0, 2, 6, 12, 18 (in T and D), 24 (in A) cycles/second in the temporal domain. Note that 24 Hz is not an even divisor of the sampling frequency; it was however chosen among the discrete set of reproducible frequencies for gathering information in the high frequencies area in the achromatic channel.

Figure 2:
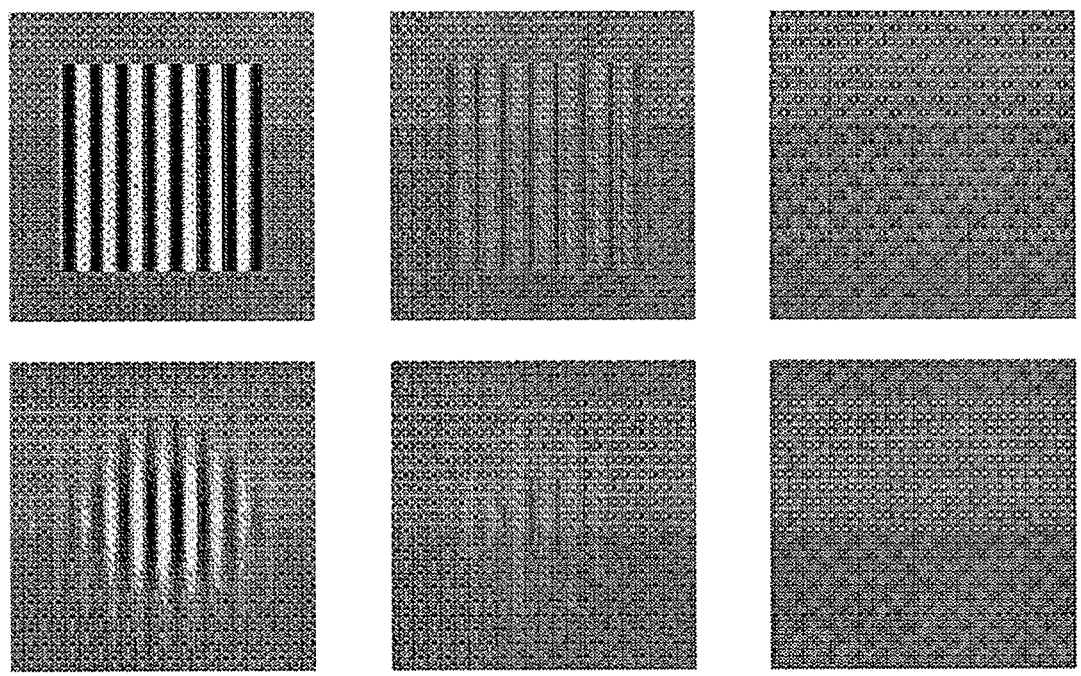
FIG. 2 are images corresponding to visual stimuli.

Gaussians that modulate the grids were chosen with standard deviations, $\alpha$, equal to about ⅙ of the image size, with this subtending about 5° by default. Considering that a gaussian tends to zero 3$\alpha$ away from its center, this choice may provide that gabor cutoffs are essentially eliminated in any direction of the space. Grids and gabors with certain spatial frequency in the cardinal directions of the color space are shown in FIG. 2.

Function g(t) is a square temporal envelope with a length $t_e$, about 1 second by default, (if the push button has not been pressed before), with gaussian smoothings at the beginning and the end of the presentation. Said smoothings, centered at $t_1$ and $t_2$, have a length equal to about 10% of the total length $t_e$. A random length pause may be introduced between presentations.

About the Tested Sectors of the Retina

The device may allow the sensitivity of the retina to be evaluated in a field of sight of up to about ±40 vertical degrees and about ±60 horizontal degrees. In order to explore different areas of the field of sight, the position of the fixation point may be modified. Particularly, with the point of fixation being at the center of the screen (position by default) the examined field of sight is about ±20 vertical degrees and about ±30 horizontal degrees, segmenting it from about 4 rows and about 6 columns (about 24 sectors) to about 8 rows and about 12 columns (about 96 sectors), removing the 4 sectors in the corners and with a specific sector for the fovea, that is, from about 21 sectors to about 93 sectors in total.

About the Experimental Determination of the Blind Spot

The measurement session may begin with the determination of the patient's blind spot position and size, according to the algorithm created for performing this task. Once the fixation stimulus suitable for the patient has been chosen, on an achromatic background with luminance being half of the monitor maximum luminance, an achromatic square stimulus test of the maximum luminance allowed by the device may be presented, subtending about 1° and with a about 1 second of total length. Test position may be varied by scanning the field of sight in a horizontal direction first and then in a vertical position, in straight lines passing through the center of an average standard individual's blind spot. The patient, looking at the fixation point, would press the push button as long as test stimulus is visible. The blind spot size may be calculated from the size of the area where the patient does not respond to the test. The center of area may be used in the step of threshold measurement for presenting the stimuli checking suspected fixation losses.

About the Measurement Method

The spatial frequency, the temporal frequency and the direction of modulation may define a measurement session. Once the position and the size of the patient's blind spot have been determined, the measurement session may begin with the occurrence of the fixation stimulus and with the display screen being turned on with the average stimulus (in one embodiment, a white default screen). The patient may be adapted for about 30 seconds to the average stimulus. Once this period of time has elapsed, the fixation stimulus may disappear and the first test may appear. The test position may randomly vary on the screen during the session, and the patient may press the push button if any spatial-temporal variation is detected with respect to the average at any position of his/her field of sight. During the session, the whole screen may remain on with the average stimulus. For a detection to be counted, the stroke may be done between $t_1$ seconds from the appearance of the stimulus and disappearance thereof. The algorithm designed for this purpose may decide, depending upon whether a stimulus is detected or not, if next time that a stimulus should be presented with a greater or smaller amplitude. In this way, all campimetry thresholds may be determined in a single session.

The observation distance is, by default, about 25 cm. Measurements may be monocular and with a pertinent refracting compensation. The patient should be able to look at the observation distance for an extended period of time without feeling discomfort, to minimize the level of effort. Measurements should be made in the dark.

About Threshold Search Strategy

Figure 4:
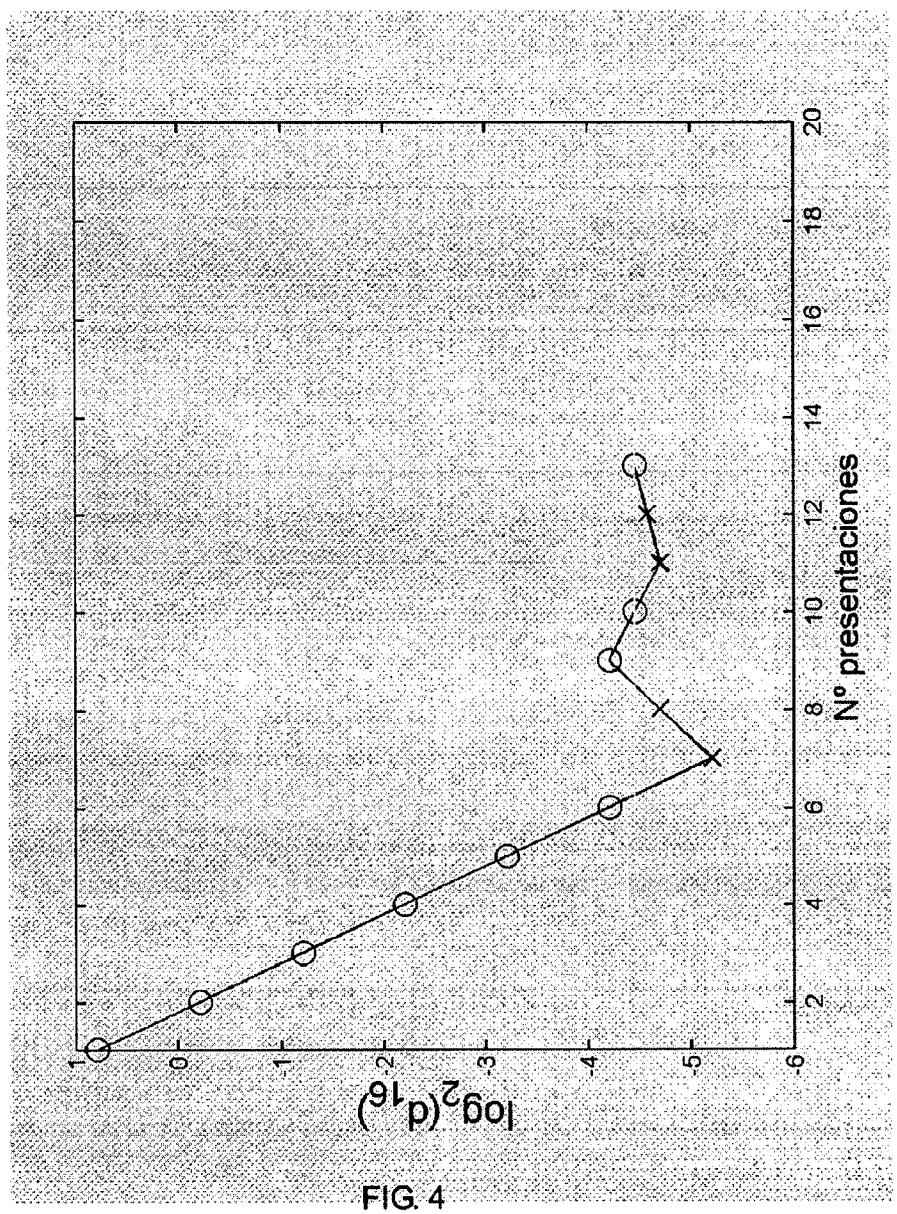
FIG. 4 is a graph showing the sensitivity threshold searching method.

The session may begin by presenting a stimulus with the maximum possible value of the amplitude, $\Delta_{MAX}$. If stimulus is detected by the patient, the amplitude may be divided by 2 and continued in this way until no detection occurs for certain value of amplitude, $\Delta_1$. A change in the direction of response is referred to as reversal. For the following presentation the amplitude may be multiplied by $\sqrt{2}$ and continued in this way until detection again occurs. After this second reversal, amplitude may be divided by $4\sqrt{2}$, and so on. Therefore, two consecutive amplitude values are related by the expression:

$$\log_2(\Delta_i) = \log_2(\Delta_{i-1}) + \frac{(-1)^{n+1}}{2^n}$$

where n is the number of reversals until position i. The process may be completed when a certain number of presentations have been reached, by default about 18 presentations (about 20 in the cardinal direction of A) or when about 4 reversals have occurred. The last detected value of the amplitude may then be allocated to threshold. FIG. 4 shows an example showing this method. The method may be interrupted if about 5 consecutive presentations with maximum amplitude in certain sector have not been detected. In this case and in any other case in which the threshold cannot be measured, the label not a number may be allocated thereto.

About the Control Stimuli

Throughout the execution of the experiment several stimuli may be semi-randomly delivered for estimating the reliability of the observer measurements:

False positive controls: null amplitude presentations for checking a possible indiscriminate activation of the push button. For a measurement session to be considered valid the false positive rate should be lower than about 33%.

False negative controls: maximum amplitude presentations appearing near the fovea for checking a possible observer's attention deficit. These controls are similar to Gabors of the measurement that is being carried out, unless their $f_x$ and $f_t$ cannot take very high values. For a measurement session to be considered valid the false negative rate should be lower than about 33%.

Fixation loss controls: presentations in the observer's blind spot. They may be about 1.5° sized squares with no Gaussian smoothing. They may have the chromatic and spatial modulation of the measurement that is being carried out, and no temporal blinking. For a measurement session to be considered valid the fixation loss rate should be lower than about 20%.

To adequately space the controls of one class in time, $\{E_1, . E_2, \ldots, E_i, \ldots E_{Nmáx}\}$ could be potentially presented to the observer as a stimulus series. A certain stimulus $E_i$ may be a threshold measurement stimulus or a control stimulus. $N_{máx}$ may represent the sum of the maximum number of presentations allowed for measuring a threshold in the total of the retina sectors to be explored in campimetry and the maximum number of control stimuli of all the types. The presentations corresponding to, for example, false negative controls may be determined by dividing the sequence of possible stimuli in as many intervals as controls of this type are desired with one of these controls being randomly locating at each interval. For example, if the potential stimuli sequence is $\{E_1, E_2, \ldots, E_i, \ldots E_{12}\}$ and about 3 false positive controls are presented, 1 may be randomly positioned in each of the three intervals bounded by $\{E_{1+4(k-1)} E_{4+4(k-1)}\}$, with k=about 1,2,3, and the two remaining stimuli of each interval would be potential stimuli for measuring the threshold or potential stimuli of false negative or fixation loss. Once the false positives have been arranged in the sequence, the rest of the controls may proceed in the same manner.

About Standard Observers

The instrument may be provided with a database that includes the results of the standard observers (observer with normal vision and with no pathologies), corresponding to campimetries in the cardinal directions of the color space, for each of the about 25 combinations of spatial and temporal frequencies generated by the device by default.

These measurements may be used for making the corresponding diagnoses.

About Result Presentation

Patient's results may be shown in the following formats:
a) For each modulation direction:
   Threshold amplitude matrix and error matrix for each of the spatial frequency and the temporal frequency combinations being examined.
   Absolute sensitivity campimetry in gray levels for each of the spatial frequency and the temporal frequency combinations examined.
   Color-coded diagnosis map according to criteria to be described in the following section.
b) For each sector of the retina and modulation direction and whenever sufficient measurements are available:
   Spatial-temporal detection surface of the channel for a particular retina sector.
   Spatial contrast sensitivity functions (CSFs) at a constant temporal frequency.
   Temporal contrast sensitivity functions (CSFs) at a constant spatial frequency.

About the Diagnosis Criteria

With the purpose of determining whether a patient's response is within the normality interval, the probability p that normal measurements (according to standard observers) exist may be determined over the measurement carried out by the patient. Thus, measurements carried out may be codified as follows: in green when said probability p is greater than about 5% ($p \geq 0.05$), yellowish green when ranging from about 5% to about 2% and (about $0.02 \leq p <$ about 0.05), yellow when ranging from about 2% to about 1% (about $0.01 \leq p <$ about 0.02), orange when ranging from about 1% to about 0.5% (about $0.005 \leq p <$ about 0.01), red when being lower than about 0.5% ($p <$ about 0.005). Remember that is not always possible to carry out measurements of the threshold. As noted above, when measurement has not been able to be carried out a not a number label may be allocated thereto.

When measurement is not a number (maximum contrast is not seen by the patient) it may be codified in blue when probability that a normal individual is also labeled for that measurement with not a number (that is, he/she does not see the maximum contrast either) is greater than or equal to about 50%. When this percentage is ranging from about 25% to about 50% it may be codified in violet. Finally, when less than about 25% of normal individuals do not see the stimulus either, it may be codified with a purple color.

About Other Embodiments

The device and method have been described referring to one embodiment, but one skilled in the art may be able to introduce variations and may be able to replace some elements by others technically equivalent, which also may be included within the scope of protection defined by the appended claims.

For example, the device could be divided into several non-integrated elements, or elements of the computer system that have been presented separately could be integrated.

What is claimed is:

1. A device to determine the contrast sensitivity of an individual's visual system through a series of tests in a measurement session, the device comprising:
   a means for producing real time digital images, corresponding to modulated visual stimuli; and
   a display means for presenting said images to an individual's eye;
   wherein said stimuli are configured in their spatial and temporal characteristics for each measurement session, and said stimuli are chosen in the cardinal directions of the color space, in which only one of the following mechanisms are able to respond to the stimulus: a non opponent or achromatic mechanism, a red-green opponency mechanism, and a blue-yellow opponency mechanism.

2. A device as claimed in claim 1, wherein the stimuli are modulated sinusoidally in time.

3. A device as claimed in claim 1, wherein the stimuli follow a pattern with spatial and temporal modulation comprising a sinusoidal grid.

4. A device as claimed in claim 3, wherein said sinusoidal grid is modulated by a two-dimensional Gaussian envelope.

5. A device as claimed in claim 3, wherein the spatial frequency of said pattern is selected from about 0 to about 20 cycles/degree.

6. A device as claimed in claim 3, wherein the temporal frequency of said pattern is between about 0 to about 30 cycles/second.

7. A device as claimed in claim 1, wherein the length of each stimulus is between about 0 to about 5 seconds.

8. A device as claimed in claim 1, wherein the colors included in the modulated stimuli in a particular direction of the color space may be selected from a 256 color palette generated for said direction.

9. A device as claimed in claim 1, wherein the device includes a camera for recording the eye position during a test of the measurement session.

10. A device as claimed in claim 1, wherein the device examines the individual's field of sight up to about 20 vertical degrees and up to about 30-horizontal degrees around a fixation point.

11. A device as claimed in claim 10, wherein the device allows the fixation point to be moved up to about 20 vertical degrees and up to about 30 horizontal degrees.

12. A device as claimed in claim 1, wherein the individual's field of sight is divided into sectors for examination purposes, establishing a specific sector for the fovea.

13. A device as claimed in claim 1, wherein said image producing means and said display means are part of a computer system that also includes a central processing unit and a memory.

14. A device as claimed in claim 13, wherein said memory comprises:
   a measurement session configuration and control routine;
   a repository of results of the measurement session;
   a repository of results obtained for individuals with no visual pathologies, referred to as standard observers;
   a visual pathology diagnosis routine from the results of the measurement session and said standard observers; and
   a displaying routine of said results and said diagnosis.

15. A method to determine the contrast sensitivity of an individual's visual system through a series of tests in a measurement session, using the device as claimed in claim 1.

16. A method as claimed in claim 15, wherein during the measurement session the position in which each test stimulus is presented to the eye may be randomly varied and the pause between one stimulus and the following one may also be randomly varied.

17. A method as claimed in claim 15, wherein the position and size of an individual's blind spot may be determined by presenting a high luminance, substantially point shaped, short visual stimulus to the individual's eye and successively moving said stimulus in horizontal and vertical directions, and wherein the individual may press a push button when the stimulus is visible to the individual, so that the blind spot position and size may be calculated from the area in which the individual does not respond to the stimulus.

18. A method to determine the contrast sensitivity of an individual's visual system through a series of tests in a measurement session, using a device to determine the contrast sensitivity of an individual's visual system through a series of tests in a measurement session, the device comprising:
   a means for producing real time digital images, corresponding to modulated visual stimuli; and
   a display means for presenting said images to an individual's eye;
   wherein said stimuli are configured in their spatial and temporal characteristics for each measurement session, and,
   wherein the measurement session comprises the steps of:
   presenting a stimulus with the maximum possible value of the amplitude;
   repeating the stimulus presentation by dividing the amplitude successively by about 2 as long as a stimulus is detected by the individual, that is, until reversal occurs;
   repeating stimulus presentation multiplying successively by about $2^{1/2}$ the amplitude from nondetection until the stimulus has been detected again by the individual, that is, until a new reversal occurs;
   carrying out both preceding steps but applying a division or multiplication factor of about $2^{2^{-n}}$, respectively, with n being the reversal number;
   finishing the session after about 4 reversals or after about 20 presentations;
   allocating the last amplitude value detected to the threshold; and
   determining the contrast sensitivity as the inverse of said threshold.

* * * * *